United States Patent [19]

Miranda

[11] 3,991,896

[45] Nov. 16, 1976

[54] STOPPER ASSEMBLY

[75] Inventor: Eduardo V. Miranda, Huntington Beach, Calif.

[73] Assignee: Baxter Travenol Laboratories, Inc., Deerfield, Ill.

[22] Filed: Nov. 27, 1974

[21] Appl. No.: 527,935

Related U.S. Application Data

[62] Division of Ser. No. 402,951, Oct. 3, 1973, Pat. No. 3,888,113.

[52] U.S. Cl. .............................................. 215/227
[51] Int. Cl.² ........................................ B65D 39/00
[58] Field of Search ............ 73/57, 209, 322.5, 427; 215/227, 200, 355; D9/254, 261, 262

[56] References Cited
UNITED STATES PATENTS

| | | | |
|---|---|---|---|
| 1,588,847 | 6/1926 | McGee | 215/355 X |
| 2,931,230 | 4/1960 | Lowery | 73/427 |
| 3,411,343 | 11/1968 | Baird, Jr. | 73/57 |
| 3,522,731 | 8/1970 | Wilson | 73/209 |
| 3,635,678 | 1/1972 | Seitz et al. | 73/57 X |
| 3,772,910 | 11/1973 | McGinn et al. | 73/57 |

FOREIGN PATENTS OR APPLICATIONS 101,407  4/1941  Sweden ........................... 215/355

*Primary Examiner*—Richard C. Queisser
*Assistant Examiner*—Joseph W. Roskos
*Attorney, Agent, or Firm*—Lawrence W. Flynn; Max D. Hensley

[57] ABSTRACT

A reagent tube and stopper assembly comprising in combination a cylindrical receptacle for containing a clot timing test reagent solution and a flexible stopper for closure thereof and dispensing a spherical member into said reagent solution by depressing a probe into an upper cavity in said stopper and against a thin membrane separating a lower sphere containing cavity in said stopper.

3 Claims, 8 Drawing Figures

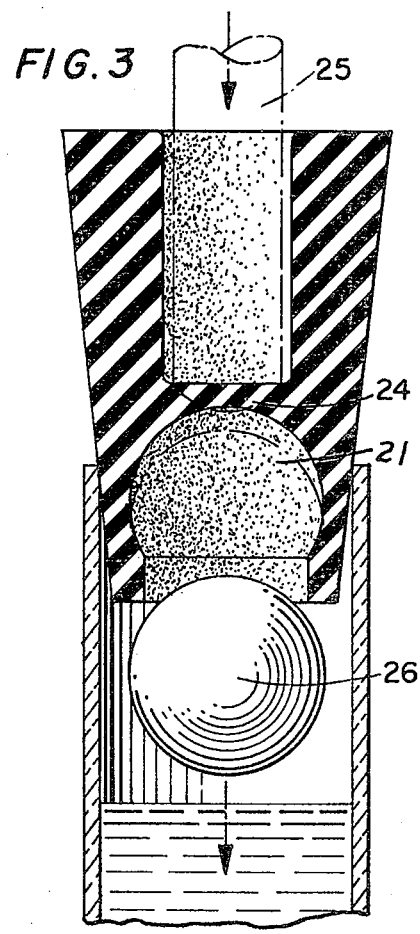
FIG. 3
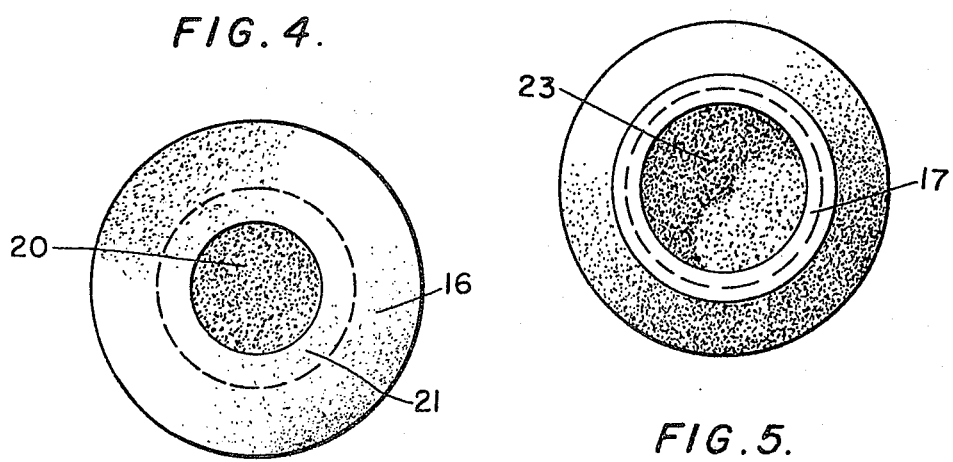
FIG. 4.
FIG. 5.

STOPPER ASSEMBLY

This is a division of application Ser. No. 402,951, filed Oct. 3, 1973, now U.S. Pat. No. 3,888,113.

This invention relates to a reagent tube and stopper assembly and, more particularly, to a stoppered reagent tube for thromboplastin and partial thromboplastin products used in the determination of blood coagulation times.

The process of blood coagulation is a complex mechanism which involves the interaction of a number of blood components or factors. If there are deficiencies in any of these components or defects in their interaction, the blood coagulation process may be altered such as to result in a failure to clot or prolongation of the clotting time.

Various tests have been devised for detecting and diagnosing blood coagulation defects and deficiencies. Among these tests are the prothrombin time determination tests such as the Quick 1-stage test, *Amer. J. Med. Sci.* 190, 501 (1935); the modified Owren 2-stage test described by Ware et al., *Amer. J. Clin. Path.* 22, 791 (1952); and the partial thromboplastin time (PTT) test described by Langdell et al., *J. Lab. and Clin Med.* 41, 637 (1953).

The prothrombin time determination tests and PTT tests employ tissue thromboplastin and partial thromboplastin materials. These materials can be obtained, for example, by extracting warm-blooded mammal brain tissue in accordance with the procedure described by Bell et al., *Nature* 174, 880 (1954). In general, these tests are carried out by admixing a plasma sample with the thromboplastin or partial thromboplastin material and calcium chloride, incubating at 37° C. and then measuring the time for clotting to occur. Further description of these tests and materials can be found, for example, in U.S. Pat. Nos. 3,179,567; 3,228,481; 3,293,134; 3,395,210; 3,486,981; and 3,522,148; and in *Amer. J. Clin. Path.* 57, 482–6 (1972); 59, 581–5 (1973).

Although these prothrombin time and PTT determination tests can be carried out manually, for mass testing purposes it is more desirable to conduct tests in automatic or semi-automatic equipment. Various types of such equipment, generally referred to as clot timers, are known. These devices determine the end point of the clotting by mechanical, electrical or similar such means.

One such recently developed clot timer determines the end point by sensing a change in viscosity of the sample. In this device, a magnetic member, such as a steel ball, is suspended within the fluid sample in a reagent tube and a magnetic field is provided through the sample which tends to hold the magnetic member in a fixed position as the sample is reciprocated. This condition obtains so long as the viscosity of the sample remains below a predetermined threshold. However, when the increased viscosity of the fluid sample is sufficient to enable the reciprocating fluid to move the steel ball away from its fixed position, and against the magnetic force tending to hold it in its fixed position, the change in the ball location in the sample is detected and the elapsed time is measured. Further description of this device can be found in U.S. Pat. No. 3,635,678.

In the latter described clot timing system, the reagent tube and the steel ball are preferably very close in diameter with only a small tolerance existing between the ball and the inner wall of the tube. In practice, it is convenient to supply the reagent tube together with the steel ball suspended in the thromboplastin or partial thromboplastin product. Due to the aforesaid small tolerance, there is a tendency of undesirable cavitation reactions occurring and homogenization of the thromboplastin material in the tube by the shaking which occurs in ordinary handling and shipment.

Accordingly, it is an object of this invention to provide an improved stoppered reagent tube for thromboplastin and partial thromboplastin products used in the determination of blood coagulation times.

Other objects and advantages of the invention will be apparent to the person skilled in the art after reading the description hereof.

Briefly stated, the reagent tube and stopper assembly of this invention comprises a receptacle for containing a reagent solution and a flexible stopper, said receptacle having a mouth and an elongated cylindrical wall, said flexible stopper having upper and lower surfaces, a generally cylindrical outer surface and upper and lower cavities, said lower cavity being generally spherical and having a downwardly disposed opening at said lower surface with a width less than the diameter of said spherical cavity, said upper cavity having an upwardly disposed opening at said upper surface and being separated from said lower cavity by a thin, flexible membrane, said outer surface being adapted for snug positioning within the inner cylindrical surface of the upper portion of said receptacle, said spherical cavity being adapted for holding a sphere having a diameter slightly less than the diameter of said receptacle.

While the specification concludes with claims particularly pointing out and distinctly claiming the subject matter regarded as forming the present invention, it is believed that the invention will be better understood from the following exemplary description taken in connection with the accompanying drawings in which:

FIG. 3 is another partial side elevational view of the reagent tube and stopper assembly in cross-section showing the operation of the device.

FIG. 4 is a top view of the reagent tube and stopper assembly.

FIG. 5 is a bottom view of the reagent tube and stopper assembly.

Figure 1:
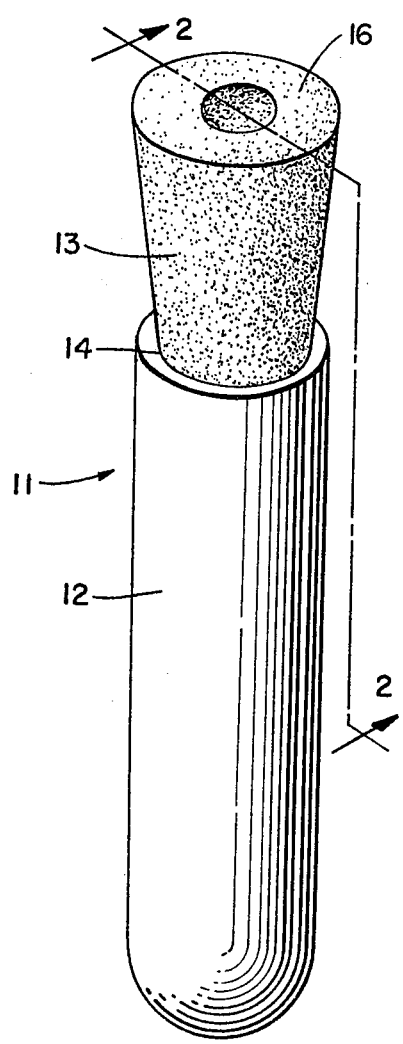
FIG. 1 is a perspective view of the reagent tube and stopper assembly of this invention.

Referring now to the drawings, particularly to FIGS. 1 to 5, the reagent tube and stopper assembly is generally indicated by 11 and comprises receptacle 12 and stopper 13. In this illustrative embodiment receptacle 12 is a test tube having a mouth 14 at the top and elongated cylindrical wall 15. Receptacle 12 is adapted for containing a reagent solution 27. Receptacle 12 can be provided with a neck, if desired, for handling purposes; and it can also be provided with a lip, if desired, for pouring purposes. Receptacle 12 preferably is made of glass or a rigid, transparent plastic.

Stopper 13 is a combination closure and retaining device. It has a generally cylindrical outer surface 18 whereby it is adapted for snug positioning within the inner cylindrical surface of the upper portion of receptacle 12 for closure of mouth 14. As used herein, the term "generally cylindrical" includes cylindrical configurations and gradually inwardly tapering structures having a frusto-conical configuration as illustrated in the drawings.

Stopper 13 is provided with two cavities. The lower cavity 21 is generally spherical and adapted for retaining a sphere, for example, a steel ball such as that described in the clot timing device of U.S. Pat. No. 3,635,678. In the clot timing method of said device it is desirable to employ a steel ball having a diameter only slightly less than the bore diameter of the reagent tube.

Lower cavity 21 has a downwardly disposed opening 23 with a neck 19 at the lower surface 17 of stopper 13. The width of opening 23 is slightly less than the diameter of cavity 21 so that sphere 26 retained therein will not fall into the lower portion of receptacle 12 without the application of an extrinsic force. However, opening 23 should be sufficiently large so that upon the application of an extrinsic force from above, the resiliency of the stopper will permit expansion of neck 19 to the extent necessary to allow sphere 26 to be pushed out of cavity 21.

Upper cavity 20 is cylindrical in this illustrative embodiment and has an upwardly disposed opening 22 at the upper surface 16 of stopper 13. Separating cavities 20 and 21 is a relatively thin, flexible membrane 24. Cavity 20 is adapted for placement therein of probe 25 which can be depressed sufficiently downwardly to deform flexible membrane 24 and thereby serve as the extrinsic force to push sphere 26 out of lower cavity 21. Probe 25 can be any conveniently available laboratory implement, preferably elongated, such as a pipette tip, a small bore tube or the end of a pencil.

Stopper 13 can be fabricated of a natural or synthetic rubber or elastomer or any flexible, resilient resinous plastic material such as, for example, vinyl, polyethylene or polypropylene plastics.

Figure 6:
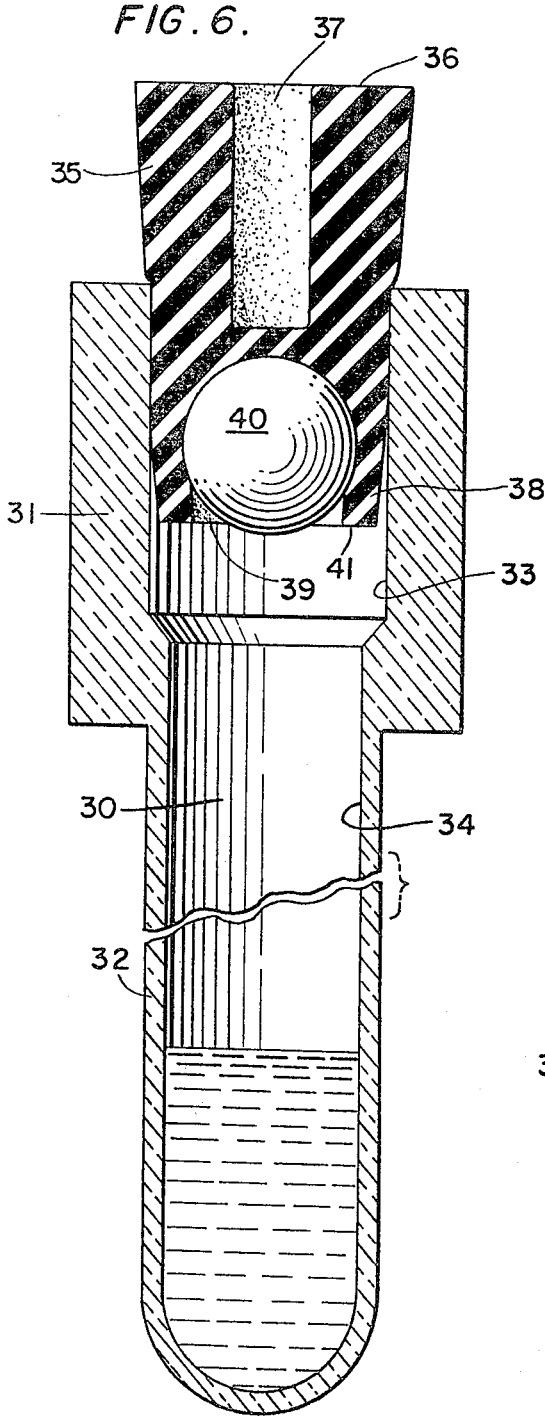
FIG. 6 is a partial side elevational view of another embodiment of the reagent tube and stopper assembly of this invention.
Figure 7:
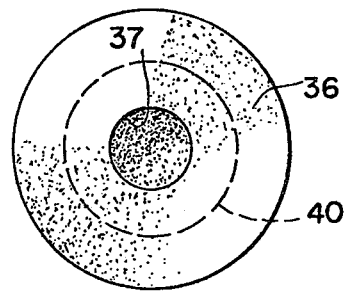
FIG. 7 is a top view of the reagent tube and stopper assembly of FIG. 6.
Figure 8:
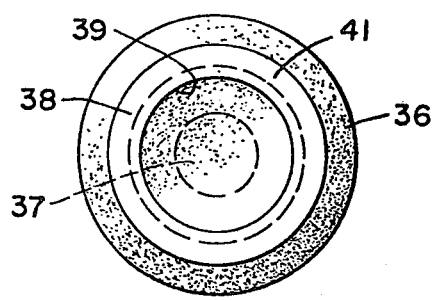
FIG. 8 is a bottom view of the reagent tube and stopper assembly of FIG. 6.

In the embodiment shown in FIGS. 6 to 8, receptacle 30 varies from receptacle 12 of the embodiment of FIGS. 1 to 5 primarily in that it is larger at the top portion than at the bottom portion in both its inner and outer diameters. Stopper 35 is essentially similar to stopper 13 of said embodiment of FIGS. 1 to 5. It has upper surface 36, lower surface 41, upper cavity 37 and contains sphere 40 in a correspondingly shaped lower cavity having opening 39.

In this embodiment of FIGS. 6 to 8, receptacle 30 is provided with an outer circumferentially disposed retaining collar 31 whereby the outer diameter of the upper portion of receptacle 30 is greater than the outer diameter of its lower cylindrical wall 32. Receptacle 30 is thereby adapted for placement and retention in a suitable clot timing apparatus such as described, for example, in U.S. Pat. No. 3,635,678. In particular, when receptacle 30 is fabricated of a lightweight plastic material, retaining collar 31 provides a desirable additional weight to the receptacle for improved seating during the vertical reciprocating motion of the clot timing test in said apparatus.

In the latter embodiment, the inner diameter of receptacle 30 is greater at upper portion 33 where stopper 35 is inserted than at the lower portion 34 where the clot timing reaction takes place. This enlarged diameter is adapted to accommodate a thickness of stopper 35 at its neck 38 such that a desired slight tolerance can be maintained between sphere 40 and the inner wall of receptacle 30 at lower portion 34 as said sphere 40 is pushed downwardly in said receptacle by a probe inserted in cavity 37.

Figure 2:
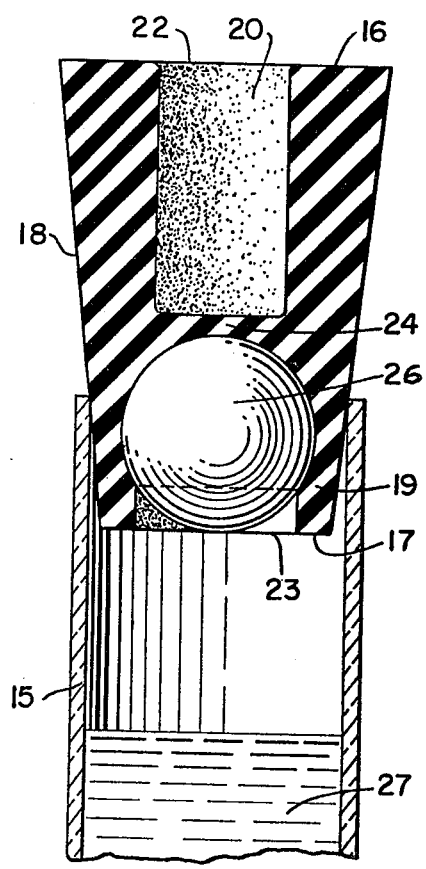
FIG. 2 is a partial side elevational view of the reagent tube and stopper assembly in cross-section taken along the line 2—2 of FIG. 1.

In the operation of the device of this invention, as can best be seen from FIGS. 2 and 3, sphere 26 will be retained in cavity 21 while stopper 13 is in the closed position in receptacle 12 and prior to the initiating of the clot timing reaction. At such time as the operator is ready to begin the clot timing test, without necessity of removing the stopper 13, probe 25 will be inserted in cavity 20 and gently depressed against membrane 24 to force sphere 26 out of cavity 21 and into fluid sample 27 contained in receptacle 12. The remaining steps of the clot timing test are then carried out in the conventional manner.

In an illustrative example of the invention, receptacle 12 is a one ml. size glass test tube with a bore diameter of about 0.22 inch. It is prefilled with about 0.1 ml. of liquid thromboplastin. Rubber stopper 13 has a height of about 0.45 inch, an upper surface diameter of about 0.315 inch and a lower surface diameter of about 0.22 inch. Cavity 20 has a cylindrical configuration about 0.125 inch in diameter and about 0.23 inch in height. Cavity 21 has a spherical configuration about 0.187 inch in diameter with its center being about 0.09 inch perpendicularly above the center of lower surface 23. Lower surface 23 has a centrally disposed opening having a diameter about 0.16 inch and a neck about 0.047 inch in height.

In another example of the invention, illustrating the embodiment shown in FIGS. 6 to 8, receptacle 30 is a one ml. size plastic test tube with a bore diameter at upper portion 33 of about 0.25 inch and a bore diameter at the lower portion 34 of about 0.198 inch. Sphere 40 retained in stopper 35 has a diameter of about 0.187 inch and thereby a slight tolerance is maintained between said sphere and the inner wall of receptacle 30 at lower portion 34 as it is pushed into the receptacle. In this example, receptacle 30 also has a circumferentially disposed retaining collar 31 about 0.6 inch high and about 0.43 inch in diameter. In other respects, the reagent tube and stopper assembly in this example is similar to that of the previous example set forth above.

It will be appreciated, of course, that the specific dimensions set forth in the foregoing examples are not to be taken as limiting the invention but are provided for exemplary purposes in describing the invention.

While particular embodiments of the invention have been illustrated and described, it will be obvious to those skilled in the art that various changes and modifications can be made without departing from the spirit and scope of the invention, and it is intended to cover in the appended claims all such changes and modifications.

What is claimed is:

1. A flexible stopper having upper and lower surfaces, a generally cylindrical outer surface with substantially straight sides and upper and lower cavities, said lower cavity being generally spherical and having a downwardly disposed opening at said lower surface with a width less than the diameter of said spherical cavity, said upper cavity having an upwardly disposed opening at said upper surface and being separated from said lower cavity by a thin, flexible membrane.

2. The flexible stopper of claim 1 in which a magnetic sphere is retained within said lower spherical cavity.

3. A flexible stopper having upper and lower surfaces, a generally cylindrical outer surface and upper and lower cavities, said lower cavity retaining a magnetic sphere, being generally spherical and having a downwardly disposed opening at said lower surface with a width less than the diameter of said spherical cavity, said upper cavity having an upwardly disposed opening at said upper surface and being separated from said lower cavity by a thin, flexible membrane.

* * * * *